(12) United States Patent
Ridgeway

(10) Patent No.: US 8,538,906 B2
(45) Date of Patent: Sep. 17, 2013

(54) SYSTEM AND METHOD FOR MEDICAL TREATMENT HYPOTHESIS TESTING USING RELATIVE LIKELIHOOD OF TREATMENT RESULTS

(75) Inventor: Gregory K. Ridgeway, Venice, CA (US)

(73) Assignee: Consolidated Research, Inc., Beverly Hills, CA (US)

( * ) Notice: Subject to any disclaimer, the term of this patent is extended or adjusted under 35 U.S.C. 154(b) by 411 days.

(21) Appl. No.: 12/815,356

(22) Filed: Jun. 14, 2010

(65) Prior Publication Data

US 2011/0099140 A1     Apr. 28, 2011

Related U.S. Application Data

(60) Provisional application No. 61/186,759, filed on Jun. 12, 2009.

(51) Int. Cl.
*G06F 17/00*     (2006.01)
*G06N 5/02*      (2006.01)

(52) U.S. Cl.
USPC ......................................................... 706/50

(58) Field of Classification Search
None
See application file for complete search history.

(56) References Cited

U.S. PATENT DOCUMENTS

| | | | |
|---|---|---|---|
| 2004/0203083 A1* | 10/2004 | Buechler et al. | 435/7.92 |
| 2006/0025931 A1 | 2/2006 | Rosen et al. | |
| 2007/0078680 A1* | 4/2007 | Wennberg | 705/2 |
| 2008/0109484 A1* | 5/2008 | Jung et al. | 707/104.1 |
| 2008/0226645 A1 | 9/2008 | O'Toole et al. | |
| 2009/0208507 A1* | 8/2009 | Rohlff | 424/139.1 |

OTHER PUBLICATIONS

Bang, Heejung, et al., "Doubly Robust Estimation in Missing Data and Causal Inference Models," Biometrics, Dec. 2005, pp. 962-972, vol. 61.
Finkle, William D., et al., "Increased Risk of Serious Injury Following an Initial Prescription for Diphenhydramine," 2002, pp. 244-250, vol. 89, Annals of Allergy, Asthma, & Immunology.
McCaffrey, Daniel F., et al., "Propensity Score Estimation with Boosted Regression for Evaluating Casual Effects in Observational Studies," Psychological Methods, 2004, pp. 403-425, vol. 9, No. 4, American Psychological Association.
Nelder, J.A., et al., "Generalized Linear Models," Journal of the Royal Statistical Society, 1972, pp. 370-384, vol. 135, No. 3, Blackwell Publishing.
PCT International Search Report completed Jul. 27, 2010 and mailed Aug. 17, 2010 from corresponding PCT Application No. PCT/US2010/038561 filed Jun. 14, 2010 (2 pages).
PCT Written Opinion of the International Searching Authority completed Jul. 27, 2010 and mailed Aug. 17, 2010 from corresponding PCT Application No. PCT/US2010/038561 filed Jun. 14, 2010 (5 pages).
Rosenbaum, Paul R., et al., "The Central Role of the Propensity Score in Observational Studies for Casual Effects," Biometricka, Apr. 1983, pp. 41-55, vol. 70, No. 1, Biometrika Trust, Great Britain.

\* cited by examiner

*Primary Examiner* — Li-Wu Chang
(74) *Attorney, Agent, or Firm* — Christie, Parker & Hale, LLP

(57) ABSTRACT

A computer-implemented system and method of evaluating the effects of medical treatments, the method including receiving patient record data; identifying relevant characteristics for evaluation; identifying a first treatment; identifying a second treatment; assigning a weight to each patient case; determining the relative likelihood, using the assigned weights, that an identified treatment will result in an identified effect when contrasted with a second identified treatment; and, outputting this estimated relative likelihood.

21 Claims, 11 Drawing Sheets

| Patient ID | T | $X_1$ | $X_2$ |
|---|---|---|---|
| 1 | 0 | A | 101.1 |
| 2 | 1 | A | 97.3 |
| 3 | 0 | B | 109.9 |
| 4 | 1 | B | 103.1 |
| 5 | 1 | B | 103.3 |

T - Treatment Indicator
- 1=exposed to the treatment,
- 0=exposed to the comparison condition $X_1$ - Categorical feature such as race, occupation, city of residence.
$X_2$ - Numeric measurement such as temperature, blood pressure, LDL.

FIG. 5A

| Patient ID | T | $X_1$ | $X_2$ | $p_i$ |
|---|---|---|---|---|
| 1 | 0 | A | 101.1 | 0.6 |
| 2 | 1 | A | 97.3 | 0.6 |
| 3 | 0 | B | 109.9 | 0.6 |
| 4 | 1 | B | 103.1 | 0.6 |
| 5 | 1 | B | 103.3 | 0.6 |

T - Treatment Indicator
 - 1=exposed to the treatment,
 - 0=exposed to the comparison condition $X_1$ - Categorical feature such as race, occupation, city of residence.
$X_2$ - Numeric measurement such as temperature, blood pressure, LDL.

$p_i$ - Propensity Score
 - The seeding propensity score for each patient is $P(T=1/X_i)$

FIG. 5B

| Patient ID | T | $X_1$ | $X_2$ | $p_i$ | T-p |
|---|---|---|---|---|---|
| 1 | 0 | A | 101.1 | 0.6 | -0.6 |
| 2 | 1 | A | 97.3 | 0.6 | 0.4 |
| 3 | 0 | B | 109.9 | 0.6 | 0.4 |
| 4 | 1 | B | 103.1 | 0.6 | -0.6 |
| 5 | 1 | B | 103.3 | 0.6 | -0.6 |

T - Treatment Indicator
- 1=exposed to the treatment,
- 0=exposed to the comparison condition $X_1$ - Categorical feature such as race, occupation, city of residence.
$X_2$ - Numeric measurement such as temperature, blood pressure, LDL.

$p_i$ - Propensity Score
- The seeding propensity score for each patient is $P(T=1/X_i)$ T-p - Residual

FIG. 5C

| Patient ID | T | $X_1$ | $X_2$ | $p_i$ | T-p | $I(X_1=A)$ | $I(X_1=B)$ | $I(X_2 \leq 97.3)$ | $I(X_2 \leq 101.1)$ | $I(X_2 \leq 103.1)$ | $I(X_2 \leq 109.9)$ |
|---|---|---|---|---|---|---|---|---|---|---|---|
| 1 | 0 | A | 101.1 | 0.6 | -0.6 | 1 | 0 | 0 | 1 | 1 | 1 |
| 2 | 1 | A | 97.3  | 0.6 |  0.4 | 1 | 0 | 1 | 1 | 1 | 1 |
| 3 | 0 | B | 109.9 | 0.6 |  0.4 | 0 | 1 | 0 | 0 | 0 | 1 |
| 4 | 1 | B | 103.1 | 0.6 | -0.6 | 0 | 1 | 0 | 0 | 1 | 1 |
| 5 | 1 | B | 103.3 | 0.6 | -0.6 | 0 | 1 | 0 | 0 | 0 | 1 |

T - Treatment Indicator
   - 1=exposed to the treatment,
   - 0=exposed to the comparison condition $X_1$ - Categorical feature such as race, occupation, city of residence.
$X_2$ - Numeric measurement such as temperature, blood pressure, LDL.

$p_i$ - Propensity Score
   - The seeding propensity score for each patient is $P(T=1/X_i)$ T-p - Residual $I(X_1=A)$ - Piecewise Constant Function for $X_1$
$I(X_1=B)$ - Piecewise Constant Function for $X_1$
$I(X_2 \leq 97.3)$ - Piecewise Constant Function for $X_2$
$I(X_2 \leq 101.1)$ - Piecewise Constant Function for $X_2$
$I(X_2 \leq 103.1)$ - Piecewise Constant Function for $X_2$
$I(X_2 \leq 109.9)$ - Piecewise Constant Function for $X_2$

FIG. 5D

| Patient ID | T | $X_1$ | $X_2$ | $p_i$ | T-p | $I(X_1=A)$ | $I(X_1=B)$ | $I(X_1=A)\times I(X_2\leq 97.3)$ | $I(X_1=A)\times I(X_2\leq 101.1)$ | $I(X_1=A)\times I(X_2\leq 103.1)$ | $I(X_1=A)\times I(X_2\leq 109.9)$ | $I(X_2\leq 97.3)$ | $I(X_2\leq 101.1)$ | $I(X_2\leq 103.1)$ | $I(X_2\leq 109.9)$ |
|---|---|---|---|---|---|---|---|---|---|---|---|---|---|---|---|
| 1 | 0 | A | 101.1 | 0.6 | -0.6 | 1 | 0 | 0 | 1 | 1 | 1 | 0 | 1 | 1 | 1 |
| 2 | 1 | A | 97.3 | 0.6 | 0.4 | 1 | 0 | 1 | 1 | 1 | 1 | 1 | 1 | 1 | 1 |
| 3 | 0 | B | 109.9 | 0.6 | 0.4 | 0 | 1 | 0 | 0 | 0 | 0 | 0 | 0 | 0 | 1 |
| 4 | 1 | B | 103.1 | 0.6 | -0.6 | 0 | 1 | 0 | 0 | 0 | 0 | 0 | 0 | 1 | 1 |
| 5 | 1 | B | 103.3 | 0.6 | -0.6 | 0 | 1 | 0 | 0 | 0 | 0 | 0 | 0 | 0 | 1 |

| Patient ID | $I(X_1=A)\times I(X_2\leq 97.3)$ | $I(X_1=A)\times I(X_2\leq 101.1)$ | $I(X_1=A)\times I(X_2\leq 103.1)$ | $I(X_1=A)\times I(X_2\leq 109.9)$ | $I(X_1=B)\times I(X_2\leq 97.3)$ | $I(X_1=B)\times I(X_2\leq 101.1)$ | $I(X_1=B)\times I(X_2\leq 103.1)$ | $I(X_1=B)\times I(X_2\leq 109.9)$ |
|---|---|---|---|---|---|---|---|---|
| 1 | 0 | 1 | 1 | 1 | 0 | 0 | 0 | 0 |
| 2 | 1 | 1 | 1 | 1 | 0 | 0 | 0 | 0 |
| 3 | 0 | 0 | 0 | 0 | 0 | 0 | 0 | 1 |
| 4 | 0 | 0 | 0 | 0 | 0 | 0 | 1 | 1 |
| 5 | 0 | 0 | 0 | 0 | 0 | 0 | 0 | 1 |

T - Treatment Indicator
 - 1=exposed to the treatment,
 - 0=exposed to the comparison condition
$X_1$ - Categorical feature such as race, occupation, city of residence.
$X_2$ - Numeric measurement such as temperature, blood pressure, LDL.
$p_i$ - Propensity Score
  - The seeding propensity score for each patient is $P(T=1/X_1)$.
T-p - Residual
$I(X_1=A)$ - Piecewise Constant Function ("PCF") for $X_1$
$I(X_1=B)$ - PCF for $X_1$
$I(X_2\leq 97.3)$ - PCF for $X_2$
$I(X_2\leq 101.1)$ - PCF for $X_2$
$I(X_2\leq 103.1)$ - PCF for $X_2$
$I(X_2\leq 109.9)$ - PCF for $X_2$ $I(X_1=A)\times I(X_2\leq 97.3)$ - Product of - PCF's for $X_1$ and $X_2$
$I(X_1=A)\times I(X_2\leq 101.1)$ - Product of - PCF's for $X_1$ and $X_2$
$I(X_1=A)\times I(X_2\leq 103.1)$ - Product of - PCF's for $X_1$ and $X_2$
$I(X_1=A)\times I(X_2\leq 109.9)$ - Product of - PCF's for $X_1$ and $X_2$
$I(X_1=B)\times I(X_2\leq 97.3)$ - Product of - PCF's for $X_1$ and $X_2$
$I(X_1=B)\times I(X_2\leq 101.1)$ - Product of - PCF's for $X_1$ and $X_2$
$I(X_1=B)\times I(X_2\leq 103.1)$ - Product of - PCF's for $X_1$ and $X_2$
$I(X_1=B)\times I(X_2\leq 109.9)$ - Product of - PCF's for $X_1$ and $X_2$

FIG. 5E

|  | Treatment cases | Comparison cases | |
|---|---|---|---|
|  |  | Before weighting | After weighting |
| depression (%) | 2.0 | 3.5 | 2.1 |
| dementia (%) | 0.3 | 1.4 | 0.3 |
| arthritis (%) | 3.8 | 6.3 | 3.9 |
| Back pain (%) | 1.9 | 3.2 | 1.9 |
| chronic mental (%) | 6.9 | 12.2 | 6.9 |
| cerebro vasc (%) | 1.8 | 3.9 | 1.8 |
| neuropathy (%) | 0.6 | 1.2 | 0.7 |
| parkinsons (%) | 0.2 | 0.4 | 0.2 |
| incontinence (%) | 0.3 | 0.6 | 0.3 |
| COPD (%) | 4.0 | 7.1 | 4.1 |
| cardiac (%) | 6.8 | 13.3 | 6.7 |
| hypertension (%) | 10.3 | 18.5 | 10.2 |
| glaucoma (%) | 2.5 | 5.0 | 2.5 |
| diabetes (%) | 3.8 | 7.0 | 3.9 |
| CRD (%) | 0.6 | 1.3 | 0.7 |
| osteo (%) | 0.4 | 0.9 | 0.4 |
| AST | 25.2 | 26.7 | 25.1 |
| ALT | 24.2 | 24.8 | 24.2 |
| LDL | 8.5 | 8.4 | 8.5 |
| HDL | 6.5 | 6.0 | 6.5 |
| Triglyc | 9.6 | 10.0 | 9.5 |
| male (%) | 31.1 | 35.3 | 31.2 |
| age (years) | 48.6 | 53.7 | 48.6 |
| AST NA (%) | 58.0 | 54.4 | 57.8 |
| ALT NA (%) | 48.2 | 47.4 | 48.2 |
| LDL NA (%) | 48.8 | 52.6 | 48.8 |
| HDL NA (%) | 39.6 | 44.8 | 39.5 |
| Triglyc NA (%) | 52.3 | 54.6 | 52.2 |

FIG. 6

| Patient ID | Period | Y | E | W | T | $X_1$ | $X_2$ |
|---|---|---|---|---|---|---|---|
| 1 | 0 | 0 | 90 | 1.0 | 0 | A | 101.1 |
| 1 | 1 | 1 | 6 | 1.0 | 0 | A | 101.1 |
| 2 | 0 | 1 | 42 | 1.0 | 1 | A | 97.3 |
| 2 | 1 | 1 | 12 | 1.0 | 1 | A | 97.3 |
| 3 | 0 | 0 | 90 | 2.0 | 0 | B | 109.9 |
| 3 | 1 | 1 | 5 | 2.0 | 0 | B | 109.9 |
| 4 | 0 | 0 | 90 | 1.0 | 1 | B | 103.1 |
| 4 | 1 | 0 | 90 | 1.0 | 1 | B | 103.1 |
| 5 | 0 | 1 | 32 | 1.0 | 1 | B | 103.3 |
| 5 | 1 | 1 | 14 | 1.0 | 1 | B | 103.3 |

Period - Period Indicator
- 1 = observation in after exposure to the treatment
- 0 = observation in the period before treatment exposure Y - Indicator of whether an identified event occurred during the observation period E - Time of the observation period or time until the identified event occurred W - Propensity Score Weight T - Treatment Indicator
- 1=exposed to the treatment,
- 0=exposed to the comparison condition $X_1$ - Categorical feature such as race, occupation, city of residence.
$X_2$ - Numeric measurement such as temperature, blood pressure, LDL.

FIG. 7

SYSTEM AND METHOD FOR MEDICAL TREATMENT HYPOTHESIS TESTING USING RELATIVE LIKELIHOOD OF TREATMENT RESULTS

CROSS-REFERENCE TO RELATED APPLICATION

This application claims the benefit of U.S. Provisional Application No. 61/186,759, filed Jun. 12, 2009, the contents of which are expressly incorporated herein by reference in its entirety.

FIELD OF THE INVENTION

The present invention relates generally to methods and systems for the statistical analysis of retrospective medical data and more specifically to methods and systems for the evaluation of the effects of medical treatments.

BACKGROUND OF THE INVENTION

There exist systems and methods for analyzing the effects of medical treatments using cohort studies. Most of these systems and methods are based on randomized controlled trials of particular treatments. Given a sufficient number of subjects over a sufficient period of time, randomized controlled trials have the advantage of simplifying this analysis by evenly distributing confounding factors (or differences between the groups) across the group receiving the treatment and the control group. These systems and methods are limited because randomized controlled trials are expensive to conduct, they rely for their accuracy in part on a high number of test subjects, and they are not very effective at identifying secondary interactions resulting from conditions that are a-typical among treatment candidates. Additionally, randomized control trials, which are prospective cohort studies, cannot capitalize on the wealth of information available in the broader set of existing patient record data in the same way that retrospective cohort studies can.

Other existing systems and methods analyze historical patient record data to evaluate the effects of particular treatments. These systems are also limited because they use a largely manual modeling process to control for confounders and patient characteristics that are not evenly distributed in the historical data across the treated group and non-treated groups. Because of the high risk of bias in these manual confounder control processes, the quality of the results produced by the existing systems are highly dependent on the operator's expertise level. Additionally, main and interaction effects associated with a high number of potential confounders in large existing data sets makes manual modeling very time intensive and subject to human error.

SUMMARY OF THE INVENTION

The invention relates to a software component system and method for the statistical analysis of patient medical records for the purpose of evaluating the relative likelihood that patient experience identified effects when treated using identified treatments. This method of analysis produces results that decision makers in the medical field can rely on to evaluate the efficacy and risks of identified treatments in determining which treatments to approve, use, and fund.

In some embodiments the system evaluates two treatments to determine the relative likelihood that patients receiving the first treatment will experience the identified effect by comparison to patients receiving the second treatment. In other embodiments, the treatments being compared are actually dosage amounts of the same treatment. In yet other embodiments, the system compares a first treatment to several different second treatments by performing several individual comparisons to produce several different ratio of rate ratios, each representing the relative likelihood that the patient will experience the identified effect as between the first treatment and another treatment.

One embodiment of the present invention provides a computer-implemented system and method of evaluating the effects of medical treatments, the method including receiving patient record data, identifying relevant characteristics for evaluation, identifying a first treatment, identifying a second treatment; assigning a weight to each patient case, determining the relative likelihood, using the assigned weights, that an identified treatment will result in an identified effect when contrasted with a second identified treatment, and outputting this estimated relative likelihood.

In another embodiment the invention relates to a system for evaluating the effects of medical treatments including: a network interface, a patient record database residing on a server accessed through a network, and a server for analysis, wherein the analysis server is configured to receive patient record data, identify relevant characteristics for evaluation, identify a first treatment, identify a second treatment, assign a weight to each patient case based on the likelihood that the patent would be a member of the exposed group, determine the relative likelihood, using the assigned weights, that an identified treatment will result in an identified effect when contrasted with a second identified treatment, and, output this estimated relative likelihood.

In another embodiment the invention relates to a server for evaluating the effects of medical treatments, the server including: a processor; and memory operably coupled to the processor storing programming instructions therein, the processor being operable to execute program instructions, the program instructions including: assigning a weight to each patient case based on the likelihood that the patent would be a member of the exposed group; using the assigned weights in determining the relative likelihood that an identified treatment will result in an identified effect when contrasted with a second identified treatment.

BRIEF DESCRIPTION OF THE DRAWINGS

FIG. 5A is an illustration of an exemplary patient case data table at the beginning of the Prepare Data in Table process of FIG. 4 according to an embodiment of the present invention;

FIG. 5B is an illustration of an exemplary patient case data table at one point in the Prepare Data in Table process of FIG. 4 according to an embodiment of the present invention;

FIG. 5C is an illustration of an exemplary patient case data table at one point in the Prepare Data in Table process of FIG. 4 according to an embodiment of the present invention;

FIG. 5D is an illustration of an exemplary patient case data table at one point in the Prepare Data in Table process of FIG. 4 according to an embodiment of the present invention;

FIG. 5E is an illustration of an exemplary patient case data table at one point in the Prepare Data in Table process of FIG. 4 according to an embodiment of the present invention;

FIG. 6 is an illustration of an exemplary table for the comparison of non-weighted patient data for patients in the treatment group and weighted patient data for patients not in the treatment group according to an embodiment of the present invention;

FIG. 7 is an illustration of an exemplary patient case data table for use in the regression modeling 118 of FIG. 1. This illustration shows the data as it is formatted during the format data for regression step 312 of FIG. 3.

Figure 1:
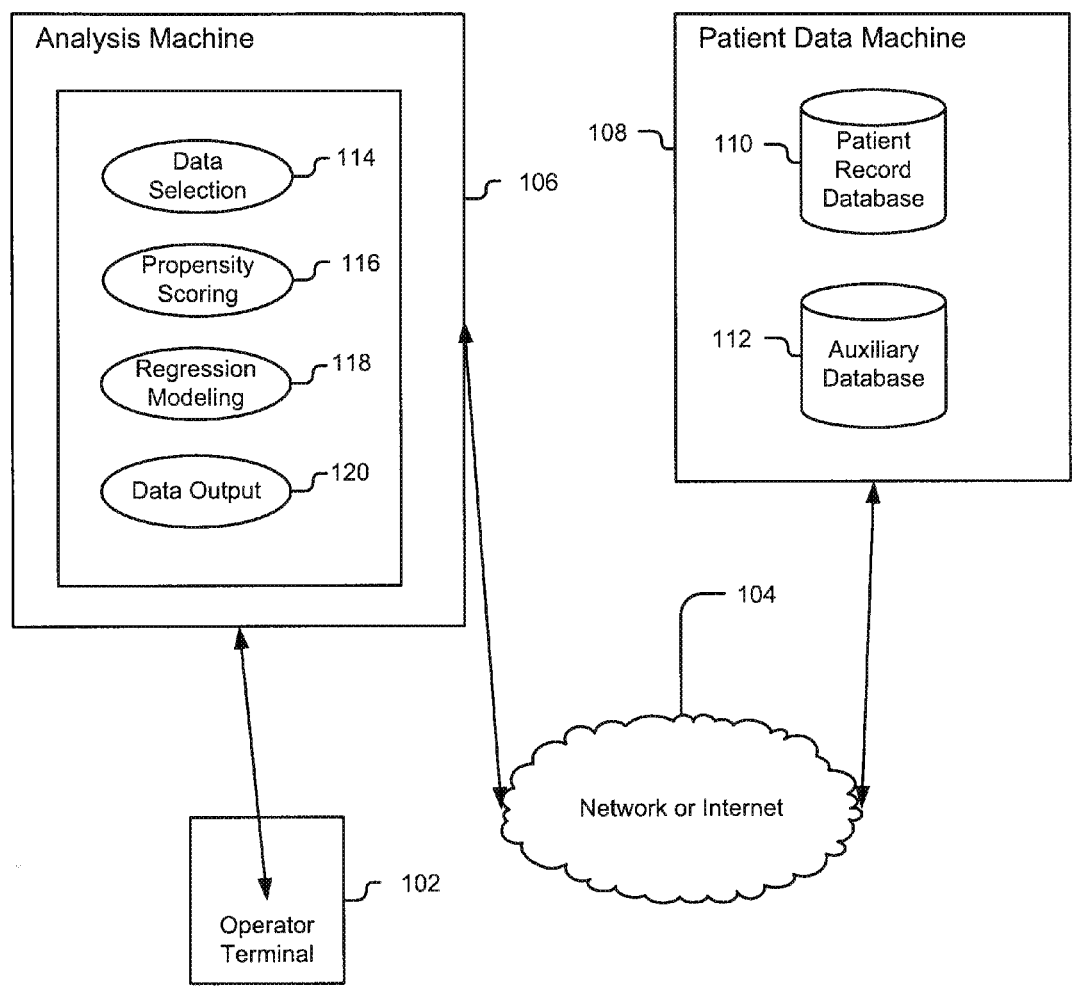
FIG. 1 is a schematic block diagram of a medical treatment hypothesis testing system constructed according to an embodiment of the present invention for comparing the effects of medical treatments based on retrospective observational data.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE INVENTION

Turning now to the drawing, embodiments of the present invention that include patient data selection, propensity scoring, inverse-probability weighting, and doubly robust estimation of the ratio of rate ratios are shown. Retrospective observational medical record data are selected by an operator from a patient record database based on two identified treatments and identified effects to be studied. Each patient who did not receive the first identified treatment is assigned a propensity score that represents the likelihood, based on the patient's individual characteristics, that the patient would have been in the group that received the first identified treatment. The assigned propensity scores are used to weight each patient's data so that the weighted data of the group that did not receive the first identified treatment (i.e. the group that received the second identified treatment) closely resembles the un-weighted data of the group that received the first treatment. The weighted data is used to perform a regression to estimate the relative likelihood that a patient receiving the first identified treatment would experience an identified effect as compared to a patient receiving the second identified treatment. This estimate is called the ratio of rate ratios. By using the weighted data in performing the regression, the estimate of the ratio of rate ratios is doubly robust.

FIG. 1 is a schematic block diagram of a medical treatment hypothesis testing system constructed according to an embodiment of the present invention for comparing the effects of medical treatments based on retrospective observational data. As shown in FIG. 1, the system includes an operator terminal 102 for operator access, over a network 104 to an analysis machine 106 and a patient data machine 108. The patient data machine 108 provides access for an operator to a patient record database 110 and an auxiliary database 112. The analysis machine 106 may include a processor; and memory operably coupled to the processor storing programming instructions and other data therein, the processor being operable to execute program instructions, a network connection to permit the analysis machine to receive input from the patient data machine 108 and other sources and to output results to the operator terminal 102 and other destinations.

The patient record database 110 stores retrospective observational patient data from patient medical records such as patient identification number, date of birth, gender, the results of medical tests, observational data recorded by healthcare providers, and information provided by patients to healthcare providers. The auxiliary database 112 stores information related to the operation of the system such as information about what records have been retrieved from the patient record database and when they were retrieved, system data formatting rules, and other data pertinent to the analysis of the patient record data.

The analysis machine 106 provides access for an operator to several software components including a data selection component 114, a propensity scoring component 116, a regression modeling component 118 and a data output component 120. These software components may take the form of computer instructions stored in computer memory and executed by a computer processor. The data selection component 114 presents the operator with an interface for the selection of relevant patient data and attributes from the patient record database 110, and retrieves and formats the selected data for use in the propensity scoring component 116.

The propensity scoring component 116 determines and assigns a propensity score to each patient record that represents that patient's likelihood of being in the group of patients receiving the identified treatment ("in the treatment group"). The propensity scoring component 116 further applies the propensity score to the patient data to weight the data of the patient records such that the weighted data for the group of patients not in the treatment group closely resembles the non-weighted data for the group of patients in the treatment group.

The regression modeling component 118 provides an interface for the operator to build and test a model for estimating the relative likelihood that a patient receiving the first identified treatment would experience an identified effect as compared to a patient receiving the second identified treatment (i.e. a patient not in the treatment group). The regression modeling component 118 receives weighted data weighted by the propensity scoring component 116.

The data output component 120 provides an interface to allow the operator to select the format and style for presenting analysis machine results. In some embodiments the data output component 120 includes a tool for selecting and formatting data produced by the analysis machine. In other embodiments the tools in the data output component 120 allow the operator to select and manipulate various visualization tools such as charts and graphs to assist interpretation and understanding of analysis machine results.

Figure 2:
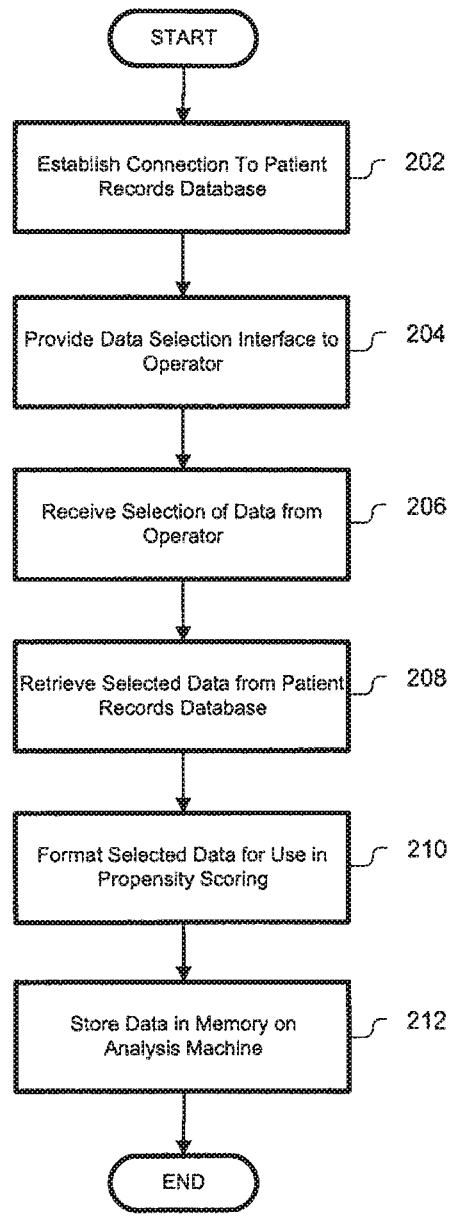
FIG. 2 is a high-level flow diagram of the steps exercised by the data selection component of the medical treatment hypothesis testing system of FIG. 1 according to an embodiment of the present invention.

FIG. 2 is a high-level flow diagram of the steps exercised by the data selection component 114 of the medical treatment hypothesis testing system of FIG. 1 according to an embodiment of the present invention. As shown in FIG. 2, the data selection component 114 initially establishes a connection to the patient record database 202 to provide access to the patient data for the operator. According to one embodiment of the invention, the component utilizes an ODBC driver to connect the data selection component 114 to the patient record database 110 on the patient data machine 108 across the network 104. The component then provides a data selection interface to the operator 204 to allow the operator to select the appropriate patient records for the subsequent analysis on the analysis machine. According to one embodiment of the invention, the data selection interface is presented to the operator as an HTML webpage viewed through a web browser application. After the operator selects the desired data, the system receives this selection 206 and retrieves the selected records 208 from the patient record database 110. The system then formats the data 210 for use in the analysis machine by the propensity scoring component and stores the formatted data 212 in memory on the analysis machine 106.

Figure 3:
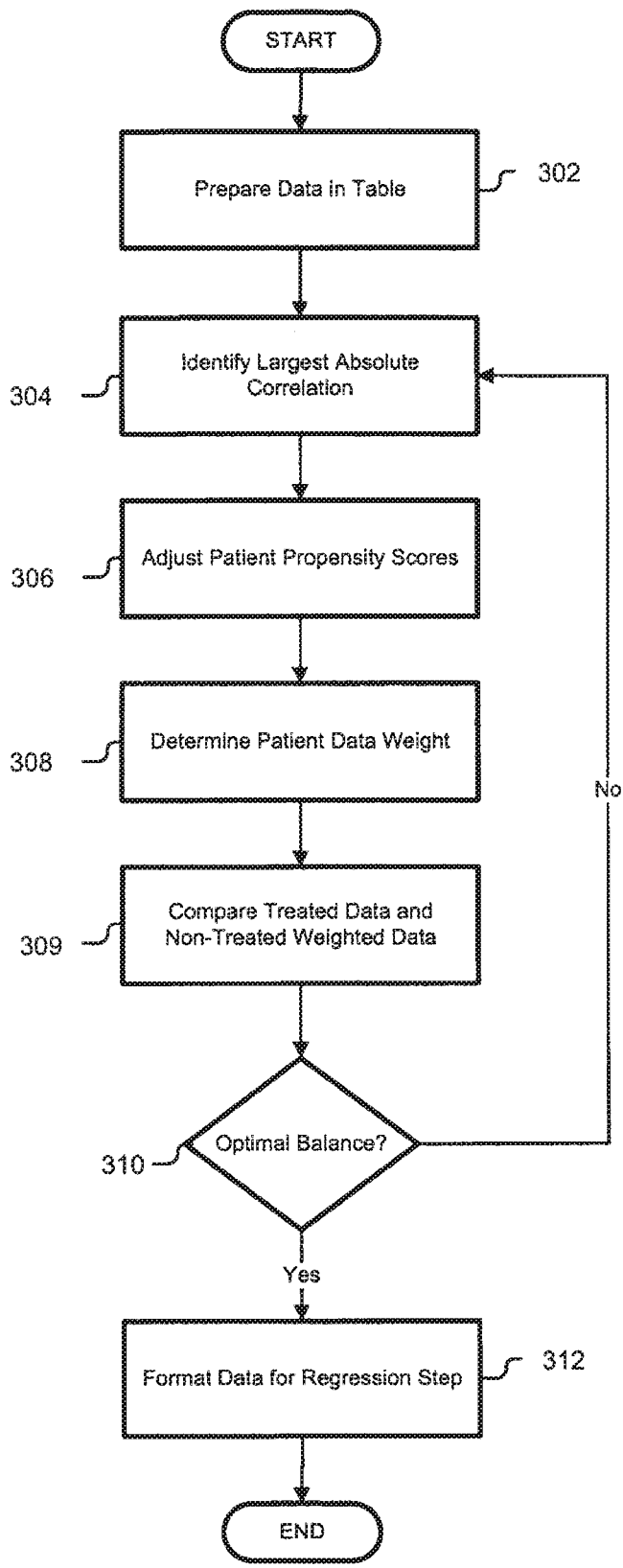
FIG. 3 is a high-level flow diagram of the steps exercised by the propensity scoring component of the medical treatment hypothesis testing system of FIG. 1 according to an embodiment of the present invention.

FIG. 3 is a high-level flow diagram of the steps exercised by the propensity scoring component 116 of the medical treatment hypothesis testing system of FIG. 1 according to an embodiment of the present invention. As FIG. 3 depicts, the propensity scoring component 116 performs an initial data preparation step 302 described in greater detail with respect to FIG. 4. In this data preparation step 302 the analysis machine prepares the patient records in a table and identifies the initial "seeding" propensity score and residual associated with each patient record, creates columns for and evaluates each indicator function and the products of indicator functions for each patient characteristic described in the selected data. After the data preparation step 302, the analysis machine identifies the largest absolute correlation 304 between any indicator function column or product of indicator functions column and the residual column. For the following formulas, $t_i$ represents the 0/1 indicator of patient i receiving the first identified treatment, $p_i$ is the estimated probability that patient i received the first identified treatment, $I_j$ is the $j^{th}$ indicator function, and n is the number of patients. To determine the extent to which any two columns are correlated, in order to identify the largest absolute correlation, the following formula is employed: $r_j = Sum_i((t_i-p_i)(I_{ji}-mean(I_j)))/((n-1)sd(t-p)sd(I_j))$. After identifying the column most correlated to the residual column, the analysis machine adjusts the propensity scores for all patients 306 based on the identified column. In adjusting the propensity scores the following formula is employed: $p_i/(1-p_i)=p_i/(1-p_i)\times exp(\delta \times sign(r_j) \times (2I_{ji}-1))$, where $\delta$ is a tuning parameter set to a small number such as 0.001. Using the new propensity score that results from the adjustment process, the analysis machine then determines a weight to apply to each of the non-treated patient records 308. The weight is calculated from the propensity score using the following formula: $w_i=p_i/(1-p_i)$.

The analysis machine compares the aggregate weighted data for patients not in the treatment group against the aggregate data for patients in the treatment group 309 to determine whether the two data sets are sufficiently similar ("optimally balanced") 310. If the data sets are not optimally balanced, the analysis machine returns to the data table, that contains newly assigned propensity scores, assigned in the adjustment process 306 and the newly calculated residual (adjusted by the change of the propensity score). The analysis machine then repeats the process of identifying the largest absolute correlation 304 with the new residual, adjusting the patient propensity scores 306, determining new patient data weights based on the newer propensity scores 308 and comparing the weighted non-treatment data with the non-weighted treatment data 309 to determine whether the data sets are now optimally balances 310. This process repeats until the data sets are sufficiently similar, at which point the analysis machine formats the data for use in the regression step 312.

Figure 4:
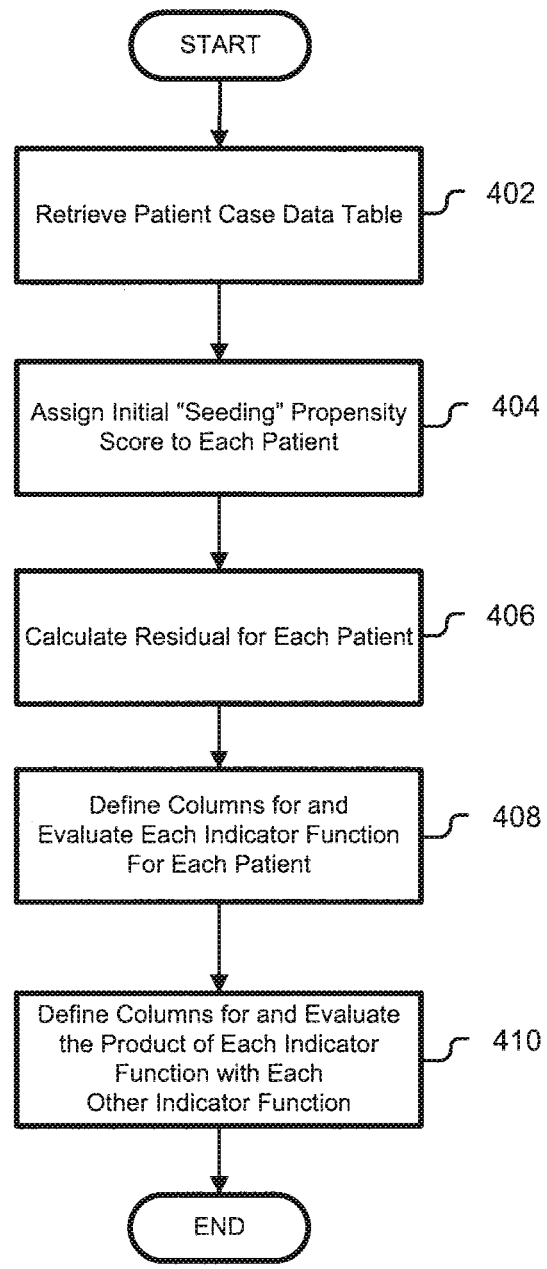
FIG. 4 is a flow diagram of the steps exercised by the Prepare Data in Table component of the propensity scoring component of FIG. 3 according to an embodiment of the present invention.

FIG. 4 is a flow diagram of the steps exercised by the Prepare Data in Table component of the propensity scoring component of FIG. 3 according to an embodiment of the present invention. The data preparation steps depicted in FIG. 4 interpret and arrange the selected patient data in a manner such that it can be interpreted by the subsequent step in the propensity scoring process involving correlation 304. The data preparation described in the foregoing steps detailed in FIG. 4 is also illustrated in exemplary tables in FIG. 5A-FIG. 5E. As FIG. 4 shows the system initially retrieves the patient case data 402 that was stored within the data selection component process 114 also depicted in detail in FIG. 2. An exemplary table containing patient case data for five example patients is illustrated in FIG. 5A. The illustration of FIG. 5A shows that each patient record at the initial stage may contain at least a patient ID number, a treatment indicator for identifying whether the patient was a member of the treatment group and data associated with categorical features such as race as well as numeric measurements such as blood pressure. Within FIG. 4, the next step in the process is the assignment of an initial "seeding" propensity score to each patient 404. In one embodiment of the invention, this seeding propensity score is calculated by the analysis machine dividing the number of patients within the treatment group by the total number of patient records. The next step in the data preparation process is the calculation of the residual for each patient record. In one embodiment of the present invention, the residual is calculated by subtracting the propensity score from the treatment indicator for each patient. Exemplary tables containing propensity score and residual data for each of the five example patients are illustrated in FIG. 5B and FIG. 5C respectively. Returning to FIG. 4, in one embodiment, the analysis machine then defines and evaluates indicator functions for each patient characteristic described in the data. The definition of said indicator functions, and creation of associated columns, is illustrated in the exemplary table of 5D that shows a new column for each condition that must be defined to allow the analysis machine to describe in boolean terms both categorical features and numeric measurements. In another embodiment the evaluation of all indicator functions is avoided by the use of published algorithmic shortcuts, in this case only selected indicator functions are defined and evaluated. The indicator functions are evaluated by determining whether the condition contained in the indicator function is true or false with respect to each patient record, with a 1 or 0 placed in the column to represent the same. The next step in the process of FIG. 4 is the definition and evaluation of the product of each indicator function with each other indicator function 410. As with the definition of the indicator functions, the system creates a new column for each condition and evaluates each condition placing a 0 or 1 in the relevant column to indicate whether the patient identified in that row meets the condition identified in the indicator function, in this case the product of one or more indicator functions, at the top of each column. The columns created by this step and the evaluation of patient records is illustrated in FIG. 5E.

FIG. 6 is an illustration of an exemplary table for the comparison of patient data for patients who received the treatment and weighted patient data for patients who did not receive the treatment according to an embodiment of the present invention. FIG. 6. illustrates the data considered in the comparison step 309 of FIG. 3 in determining whether the data has reached an optimal balance 310. The data in the exemplary table of FIG. 6 shows a sufficiently balanced data set after weighting to prepare the data for use in regression 312. The sufficiently balanced data set in the exemplary table of FIG. 6 has a maximum absolute difference less than or equal to 0.2 percent as between corresponding patient data of the aggregate weighted data for patients not in the treatment group and the aggregate data for patients in the treatment group.

FIG. 7 is an illustration of an exemplary patient case data table for use in the regression modeling 118 of FIG. 1. This illustration shows the data as it is formatted during the format data for regression step 312 of FIG. 3. In this example the original data from FIG. 5A is supplemented with data on the observed identified effects. The table of FIG. 7 shows two records for each patient, one for a "pre-treatment period" and one for a "post-treatment period." The "period" column of FIG. 7 contains a 1 or 0 to indicate whether the record describes the "post-treatment" or "pre-treatment" period respectively. The table of FIG. 7 also contains an column/indicator "Y" that indicates whether the patient experienced the identified effect during the observation period, and a column/indicator "E" that describes the length of the observation period for each patient. The table of FIG. 7. also includes a column/indicator for propensity score weight, "W" computed by the system 308 as depicted in FIG. 3 and described above.

The relative likelihood of a patient receiving the first treatment experiencing the identified effect when compared with a patient receiving the second treatment is calculated by estimating the ratio of rate ratios. The ratio of rate ratios ("RRR") compares the rates of the identified event in the pre-treatment period to the post-treatment period for the treatment (first treatment) and non-treatment (second treatment) groups. The formula for calculating the RRR is: (rate(post,treatment)/rate(pre,treatment))/(rate(post,non-treatment)/rate(pre,non-treatment)). After calculation, the analysis machine outputs this estimated RRR to the operator terminal or another location where it may be used to evaluate the relative efficacy and risks of the first and second identified treatments. Decision makers in the medical field may utilize the estimated RRR output from the analysis machine to determine whether to approve or recommend particular treatments for patients and healthcare organizations.

To adjust for potential confounding the system obtains a doubly robust adjusted ratio of rate ratios by estimating a weighted Poisson regression model 118 as shown in FIG. 1. The estimates are derived from maximizing the equation $L(b, \beta) = \text{Sum}_i \; W_i(Y_i \; f_i - \exp(f_i))$ where $f_i = \log(E_i) + b_0 + b_1 T_i + b_2 \text{Period}_i + b_3 T_i * \text{Period}_i + \beta'X$. The resulting value of $\exp(b_3)$ is the doubly robust adjusted ratio of rate ratios.

After calculation, the analysis machine outputs the doubly robust adjusted ratio of rate ratios to the operator terminal for review by the operator, or to another location where it may be used to evaluate the relative efficacy and risks of the first and second identified treatments. Decision makers in the medical field may utilize this doubly robust adjusted ratio of rate ratios output from the analysis machine to determine whether to approve or recommend particular treatments for patients and healthcare organizations.

Although the present invention has been described through the use of exemplary embodiments, it will be appreciated by those of skill in the art that various modifications may be made to the described embodiments that fall within the scope and spirit of the invention as defined by the claims and their equivalents appended hereto.

What is claimed is:

1. A computer-implemented method of evaluating the effects of medical treatments comprising:
   receiving patient record data;
   identifying relevant characteristics for evaluation;
   identifying a first treatment;
   identifying a second treatment;
   identifying an exposed group;
   assigning a weight to each patient case based on the likelihood that the patient would be a member of the exposed group;
   determining the relative likelihood that an identified treatment will result in an identified effect when contrasted with a second identified treatment, using the weighted data to perform a regression; and
   outputting this estimated relative likelihood,
   wherein the weighted data of the group that receives the second identified treatment and the un-weighted data of the group that received the first identified treatment are balanced, and
   wherein the weights are adjusted based on the estimated probability that the patient receives the first identified treatment if the balance is not reached.

2. The method of claim 1, wherein the weight assigned to each patient case is calculated by matching the patients traits and combinations of traits to a target population.

3. The method of claim 2, wherein a Poisson regression is performed.

4. The method of claim 3, wherein at least some of the traits matched are used as covariates in the regression.

5. A system for evaluating the effects of medical treatments comprising:
   a network interface;
   a patient record database residing on a server accessed through a network; and
   a server for analysis, wherein the analysis server is configured to:
   receive patient record data;
   identify relevant characteristics for evaluation;
   identify a first treatment;
   identify a second treatment;
   identify an exposed group;
   assign a weight to each patient case based on the likelihood that the patent would be a member of the exposed group;
   determine the relative likelihood that an identified treatment will result in an identified effect when contrasted with a second identified treatment, using the weighted data to perform a regression; and
   output this estimated relative likelihood,
   wherein the weighted data of the group that receives the second identified treatment and the un-weighted data of the group that received the first identified treatment are balanced, and
   wherein the weights are adjusted based on the estimated probability that the patient receives the first identified treatment if the balance is not reached.

6. An analysis server for evaluating the effects of medical treatments comprising:
   a processor;
   and a memory operably coupled to the processor storing programming instructions therein, the processor being operable to execute program instructions, the program instructions including:
   receiving patient record data;
   identifying relevant characteristics for evaluation;
   identifying a first treatment;
   identifying a second treatment;
   identifying an exposed group;
   assigning a weight to each patient case based on the likelihood that the patent would be a member of the exposed group;
   determining the relative likelihood that an identified treatment will result in an identified effect when contrasted with a second identified treatment, using the weighted data to perform a regression; and
   outputting this estimated relative likelihood, wherein the weighted data of the group that receives the second identified treatment and the un-weighted data of the group that received the first identified treatment are balanced, and wherein the weights are adjusted based on the estimated probability that the patient receives the first identified treatment if the balance is not reached.

7. A computer-implemented method of evaluating effects of medical treatments comprising:

receiving patient record data of a plurality of patients;
identifying relevant characteristics for evaluation;
identifying a first treatment;
identifying a second treatment;
identifying an effect;
identifying, from among the patients, a first group of patients who received the first treatment;
identifying, from among the patients, a second group of patients who did not receive the first treatment;
assigning a weight to the patient record data of each patient of the second group of patients corresponding to a likelihood that the corresponding patient would have received the first treatment to generate weighted patient record data of the second group of patients;
determining whether the weighted patient record data of the second group of patients is balanced with the patient record data of the first group of patients;
adjusting the weight assigned to the patient record data of each patient of the second group of patients to balance the weighted patient record data of the second group of patients with the patient record data of the first group of patients;
determining an estimated relative likelihood, using the weighted patient record data of the second group of patients to perform a regression, that the first treatment, as compared to the second treatment, will result in the effect; and
outputting estimated relative likelihood.

8. The method of claim 7, wherein determining the estimated relative likelihood that the first treatment, as compared to the second treatment, will result in the effect further comprises using the patient record data of the first group of patients, which is unweighted, in the regression.

9. The method of claim 7, wherein the likelihood that the corresponding patient would have received the first treatment is based on the relevant characteristics of the patient record data of the corresponding patient.

10. The method of claim 7, wherein assigning the weight to the patient record data of each patient of the second group of patients comprises setting a propensity score and a residual value for the patient record data of each of the patients.

11. The method of claim 10,
wherein the patient record data comprises columns of indicator functions based on the relevant characteristics, each of the indicator functions being associated with a corresponding one of the patients,
wherein the residual value for the patient record data of each of the patients is arranged in a residual value column, each place in the column corresponding to one of the patients, and
wherein assigning the weight to the patient record data of each patient of the second group of patients further comprises:
identifying which column of the indicator functions is most correlated to the residual value column;
adjusting the propensity score for the patient record data of each of the patients based on the identified column; and
determining the weight to assign to the patient record data of each patient of the second group of patients based on the propensity score.

12. The method of claim 11, wherein when identifying which column of the indicator functions is most correlated to the residual value column, the following equation is used:

$$r_j = \text{Sum}_i((t_i - p_i)(I_{ji} - \text{mean}(I_j)))/((n-1)sd(t-p)sd(I_j)).$$

13. The method of claim 11, wherein when adjusting the propensity score of the patient record data of each of the patients based on the identified column, the following equation is used:

$$p_i/(1-p_i) = p_i/(1-p_i)\exp(\delta \text{sign}(r_j)(2I_{ji} - 1)).$$

14. The method of claim 11, wherein when determining the weight to assign to the patient record data of each patient of the second group of patients based on the propensity score, the following formula is used:

$$w_i = p_i/(1-p_i).$$

15. The method of claim 11, wherein the adjusting the weight assigned to the patient record data of each patient of the second group of patients to balance the weighted patient record data of the second group of patients with the patient record data of the first group of patients comprises:
adjusting the residual value of the patient record data of each of the patients based on the propensity score;
identifying which column of the indicator functions is most correlated to the residual value column;
adjusting the propensity score for the patient record data of each of the patients based on the identified column; and
determining the weight to assign to the patient record data of each patient of the second group of patients based on the propensity score.

16. The method of claim 10, further comprising setting a treatment identifier in the patient record data of each of the patients,
wherein the treatment identifier of the patient record data of each of the first group of patients is set to 1,
wherein the treatment identifier of the patient record of each of the second group of patients is set to 0,
wherein the propensity score of the patient record data of each of the patients is initially set to be equal to the number of patients in the first group of patients divided by the total number of patients in the patient record, and
wherein the residual value of the patient record data of each of the patients is initially set by subtracting the corresponding propensity score from the corresponding treatment identifier.

17. The method of claim 7, wherein the determining whether the weighted patient record data of the second group of patients is balanced with the patient record data of the first group of patients comprises:
aggregating the patient record data of the first group of patients to generate aggregate first data;
aggregating the weighted patient record data of the second group of patients to generate aggregate second data; and
comparing the aggregate first data to the aggregate second data.

18. The method of claim 17, wherein the determining whether the weighted patient record data of the second group of patients is balanced with the patient record data of the first group of patients further comprises:
determining that the weighted patient record data of the second group of patients is balanced with the patient record data of the first group of patients when the aggregate first data is substantially similar to the aggregate second data.

19. The method of claim 18, wherein the aggregate first data is substantially similar to the aggregate second data when a maximum absolute difference between corresponding ones of the relevant characteristics of the first aggregate data and the second aggregate data is less than or equal to 0.2 percent.

20. The method of claim 7, wherein the estimated relative likelihood that the first treatment, as compared to the second treatment, will result in the effect is determined by estimating a ratio of rate ratios.

21. The method of claim 20, further comprising adjusting the estimated relative likelihood that the first treatment, as compared to the second treatment, will result in the effect is determined by estimating a weighted Poisson regression model.

* * * * *